(12) United States Patent
Biedermann et al.

(10) Patent No.: US 11,602,377 B2
(45) Date of Patent: *Mar. 14, 2023

(54) RECEIVING PART FOR COUPLING A ROD TO A BONE ANCHOR

(71) Applicant: BIEDERMANN TECHNOLOGIES GMBH & CO. KG, Donaueschingen (DE)

(72) Inventors: Lutz Biedermann, Villingen (DE); Bernd Fischer, Bräunlingen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/090,095

(22) Filed: Nov. 5, 2020

(65) Prior Publication Data

US 2021/0145485 A1    May 20, 2021

Related U.S. Application Data

(60) Provisional application No. 62/935,234, filed on Nov. 14, 2019.

(30) Foreign Application Priority Data

Nov. 14, 2019  (EP) ..................... 19209268

(51) Int. Cl.
*A61B 17/70*    (2006.01)
(52) U.S. Cl.
CPC ...... *A61B 17/7037* (2013.01); *A61B 17/7034* (2013.01)
(58) Field of Classification Search
CPC ............ A61B 17/7001; A61B 17/7032; A61B 17/7035; A61B 17/7037; A61B 17/7038;
(Continued)

(56) References Cited

U.S. PATENT DOCUMENTS

| 5,549,608 A | 8/1996 | Errico et al. |
| 5,728,098 A * | 3/1998 | Sherman ............ A61B 17/7032 606/269 |

(Continued)

FOREIGN PATENT DOCUMENTS

DE    20 2011 051 211 U1    12/2011

OTHER PUBLICATIONS

Extended European Search Report for Application No. 19209268.2, dated May 25, 2020, 10 pages.

*Primary Examiner* — Lynnsy M Summitt
(74) *Attorney, Agent, or Firm* — Lewis Roca Rothgerber Christie LLP

(57) ABSTRACT

A bone anchoring device includes a receiving part with a head receiving portion defining a seat for pivotably receiving a head of a bone anchor, and a rod receiving portion defining a recess for receiving a rod, the recess forming two legs each having an engagement surface for engaging a locking device to lock the rod in the recess, and an expansion limiting member having a surface configured to engage a portion of the receiving part spaced apart from the engagement surfaces of the legs. When the legs are urged radially outwardly, the head receiving portion is urged radially inwardly to compress and lock the head. The expansion limiting member is adjustable from a first configuration relative to the receiving part where the head receiving portion is expandable to permit the insertion of the head, to a second configuration where expansion of the head receiving portion is restricted.

21 Claims, 12 Drawing Sheets

(58) Field of Classification Search
CPC ............ A61B 17/7041; A61B 17/7043; A61B 17/7046; A61B 17/7049–7052; A61B 17/7007; A61B 17/701
See application file for complete search history.

(56) References Cited

U.S. PATENT DOCUMENTS

| | | | | |
|---|---|---|---|---|
| 6,254,602 B1* | 7/2001 | Justis | ........... | A61B 17/7032 606/272 |
| 6,273,888 B1* | 8/2001 | Justis | ........... | A61B 17/7032 606/272 |
| 6,371,957 B1* | 4/2002 | Amrein | ........... | A61B 17/7032 606/270 |
| 6,918,911 B2* | 7/2005 | Biedermann | ...... | A61B 17/7032 606/266 |
| 7,090,674 B2* | 8/2006 | Doubler | ........... | A61B 17/7032 606/277 |
| 7,316,684 B1* | 1/2008 | Baccelli | ........... | A61B 17/7037 606/86 A |
| 7,530,992 B2* | 5/2009 | Biedermann | ...... | A61B 17/7032 606/272 |
| 7,699,876 B2* | 4/2010 | Barry | ........... | A61B 17/7037 606/266 |
| 8,016,862 B2* | 9/2011 | Felix | ........... | A61B 17/7032 606/270 |
| 8,092,503 B2* | 1/2012 | Felix | ........... | A61B 17/7041 606/267 |
| 8,192,470 B2* | 6/2012 | Biedermann | ...... | A61B 17/7034 606/265 |
| 8,262,704 B2* | 9/2012 | Matthis | ........... | A61B 17/7032 606/264 |
| 8,308,776 B2* | 11/2012 | Abdou | ........... | A61B 17/8605 606/279 |
| 8,506,601 B2* | 8/2013 | Gephart | ........... | A61B 17/7035 606/266 |
| 8,506,609 B2* | 8/2013 | Biedermann | ...... | A61B 17/7037 606/306 |
| 8,876,874 B2* | 11/2014 | Abdou | ........... | A61B 17/7038 606/305 |
| 8,974,501 B2* | 3/2015 | Dikeman | ........... | A61B 17/7037 606/267 |
| 9,066,759 B2* | 6/2015 | Biedermann | ...... | A61B 17/7037 |
| 9,144,441 B2* | 9/2015 | Biedermann | ...... | A61B 17/7076 |
| 9,320,546 B2* | 4/2016 | Keyer | ........... | A61B 17/7037 |
| 9,456,851 B2* | 10/2016 | Richelsoph | ........ | A61B 17/7035 |
| 9,498,254 B2* | 11/2016 | Spratt | ........... | A61B 17/7037 |
| 9,561,058 B2* | 2/2017 | Lange | ........... | A61B 17/7032 |
| 9,895,171 B2* | 2/2018 | Webb | ........... | A61B 17/7037 |
| 10,512,487 B2* | 12/2019 | Jackson | ........... | A61B 17/7037 |
| 2005/0080415 A1* | 4/2005 | Keyer | ........... | A61B 17/7038 606/278 |
| 2006/0161152 A1* | 7/2006 | Ensign | ........... | A61B 17/7037 606/278 |
| 2006/0200128 A1* | 9/2006 | Mueller | ........... | A61B 17/7037 606/308 |
| 2007/0093826 A1* | 4/2007 | Hawkes | ........... | A61B 17/7037 606/279 |
| 2008/0312655 A1* | 12/2008 | Kirschman | ........ | A61B 17/7032 606/308 |
| 2009/0069852 A1 | 3/2009 | Farris et al. | | |
| 2009/0105756 A1* | 4/2009 | Richelsoph | ........ | A61B 17/7035 606/246 |
| 2010/0004694 A1* | 1/2010 | Little | ........... | A61B 17/7037 606/308 |
| 2010/0131017 A1* | 5/2010 | Farris | ........... | A61B 17/7038 606/308 |
| 2011/0276098 A1* | 11/2011 | Biedermann | ...... | A61B 17/7037 606/305 |
| 2014/0277163 A1* | 9/2014 | Kretzer | ........... | A61B 17/7041 606/278 |
| 2015/0272626 A1* | 10/2015 | Spratt | ........... | A61B 17/7037 606/265 |
| 2017/0135732 A1* | 5/2017 | Jackson | ........... | A61B 17/7076 |
| 2018/0243009 A1* | 8/2018 | Bobbitt | ........... | A61B 17/7037 |

* cited by examiner

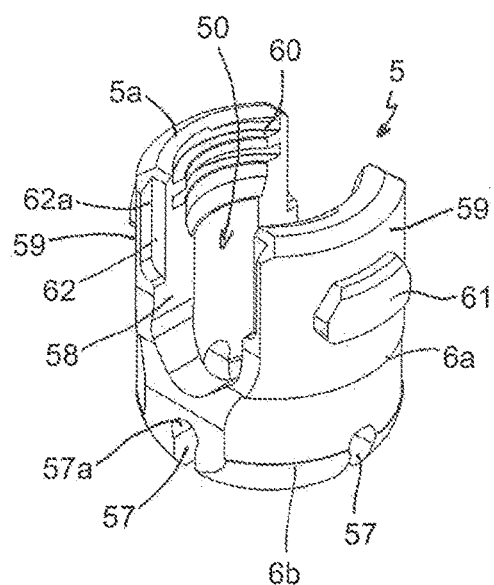
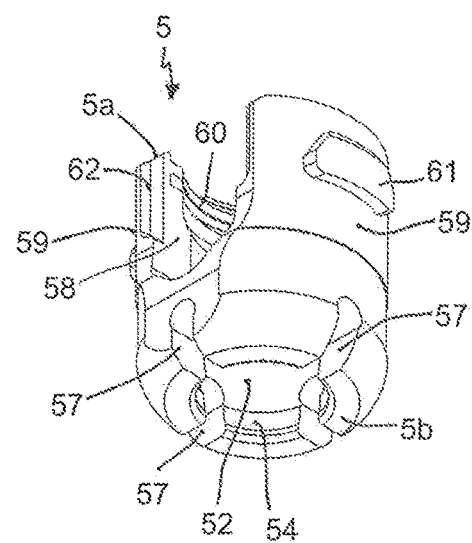
Fig. 4
Fig. 5
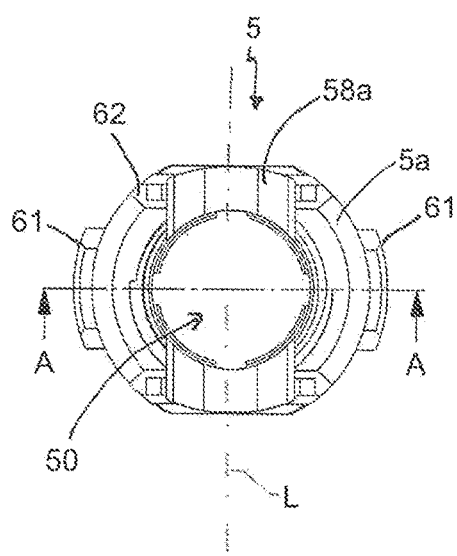
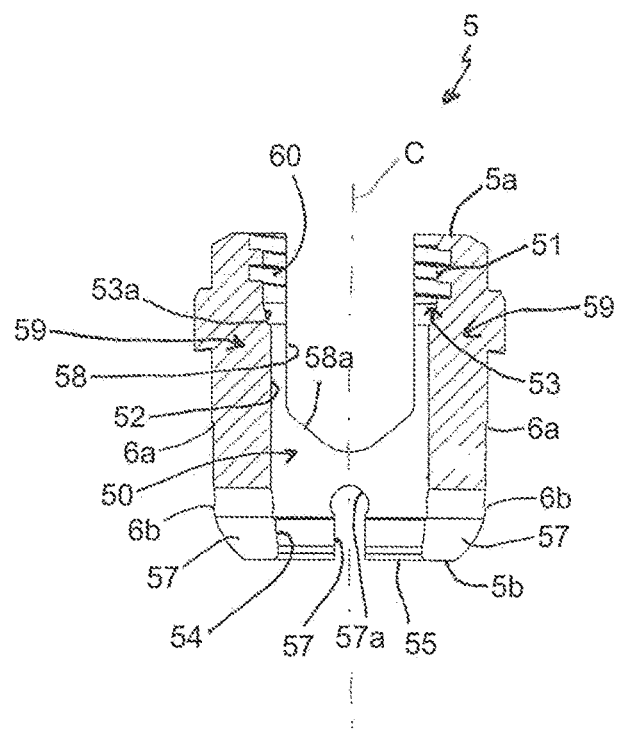
Fig. 6
Fig. 7

RECEIVING PART FOR COUPLING A ROD TO A BONE ANCHOR

CROSS-REFERENCE TO RELATED APPLICATION(S)

The present application claims priority to and the benefit of U.S. Provisional Patent Application No. 62/935,234, filed Nov. 14, 2019, the contents of which are hereby incorporated by reference in their entirety, and claims priority from European Patent Application EP 19 209 268.2, filed Nov. 14, 2019, the contents of which are hereby incorporated by reference in their entirety.

BACKGROUND

Field

The application relates to a receiving part for coupling a rod to a bone anchor, and in particular to a polyaxial bone anchoring device in which the bone anchor can be locked at an angular position without using a separate compression member.

Description of Related Art

A polyaxial bone anchoring device of this type is known, for example, from U.S. Pat. No. 7,530,992 B2. The known polyaxial bone anchoring device includes a receiver part for articulated connection of a bone anchoring element with a rod. The bone anchoring element has a shank part and a head and the receiver part has an opening for inserting the shank part with head and a recess for forming a channel for receiving the rod. Two slit-shaped recesses are formed at the lower part of the receiving part to provide elasticity to clamp the head. The head is locked in its position by the action of a force which tends to move apart the legs and which in turn leads to a compression of the receiver part.

Another bone anchor assembly is known from U.S. Pat. No. 9,498,254 B2. The known receiver member is bottom-loading and can include a seat having an opening that can be selectively increased and decreased in size so as to allow a bone anchor to be bottom-loaded. A closure element can be coupled to the receiver member and can apply a force to decrease a size of the seat and a size of the opening, angularly fixing the receiver member relative to the bone anchor.

SUMMARY

While the known polyaxial bone anchoring devices described above can lock a head of a bone anchor in a receiving part, there remains a need for a polyaxial bone anchoring device that can provide a safe locking of a head in a receiving part with a minimum number of parts, while also allowing for a variety of options for surgical correction steps.

According to an embodiment, a receiving part for coupling a rod to a bone anchor includes a head receiving portion with an interior seat for pivotably receiving a head of the bone anchor, and a rod receiving portion with a recess forming a channel with a bottom for receiving the rod, the recess forming two open legs. The head receiving portion is expandable to permit insertion of the head and is compressible to lock an inserted head in the seat. In addition, an expansion limiting member configured to encompass at least part of the head receiving portion can be provided at an outer side of the head receiving portion. When the legs are spread apart, the head receiving portion is compressed to exert a locking force onto an inserted head.

The receiving part is configured to clamp and lock the head without using an extra part such as a compression member that is usually placed on top of the head. Therefore, the receiving part is more easy to manufacture compared to receiving parts with compression members.

The locking of the head can be effected by a locking device inserted from the top end into the receiving part that cooperates with the receiving part to spread apart the legs. The locking device remains in the receiving part for finally lock the polyaxial bone anchoring device. Alternatively, the locking can be effected by using an instrument that spreads apart the legs of the receiving part. When using an instrument, the locking is temporary. A separate locking device may be used to finally lock the polyaxial bone anchoring device. Thus, with one receiving part, a variety of different surgical steps can be carried out, which considerably increases the versatility of the polyaxial bone anchoring device.

In one embodiment, the expansion limiting member is a ring. Such a part is easy to manufacture.

The receiving part can be used together with the bone anchor as a modular screw, which allows selection of an appropriate one of several bone anchors that may differ, for example, in length, size, and/or shape of the shank. In particular, a bottom loading bone anchoring device can be assembled, where the head of the bone anchor is inserted from a bottom end of the receiving part.

In a further embodiment, the expansion limiting member is configured to pre-lock an inserted head in the receiving part. As a consequence, the head cannot be removed even if it is not yet locked.

In a further embodiment, the expansion limiting member exerts a friction force onto a head inserted in the receiving part. As a consequence, the bone anchor can be maintained at a desired angular orientation prior to locking the bone anchor with respect to the receiving part.

In a further embodiment, the receiving part includes a rod support surface that is configured to support rods of different diameter in a safe manner. In particular, the rod support surface may have two inclined surfaces that hold the rod between them. In such a case, force components may be generated that further increase the locking force on the head.

In a further embodiment, the seat may extend slightly above a region with a largest outer diameter of the head so that the head can be provisionally held in the seat.

In a further embodiment, a system including a receiving part and an instrument is provided, wherein the instrument is configured to spread apart the legs of the receiving part so as to compress the head receiving portion. By means of this, the head can be provisionally locked in the head receiving part by the instrument without a locking device and/or a rod being inserted into the channel for the rod.

A still further system including a receiving part and an instrument is provided in which the instrument is configured to act directly on an inserted head in the head receiving portion to provisionally lock an angular position of the head. This also permits the head to be provisionally locked during surgical steps.

In a still further embodiment, a receiving part for coupling a rod to a bone anchor includes a head receiving portion with an interior seat for pivotably receiving a head of the bone anchor, and a rod receiving portion with a recess forming a channel with a bottom for receiving the rod, the recess forming two open legs. The head receiving portion is expandable to permit insertion of the head and is compressible to lock an inserted head in the seat. An engagement surface is provided in the rod receiving portion that is configured to be engaged by an engagement surface on a spreading member to spread apart the legs. When the legs are spread apart, the head receiving portion is compressed to exert a locking force onto an inserted head. The spreading member may be a lower edge of a locking device or a portion of an instrument. The engagement surfaces may include surfaces on the receiving part and the spreading member with different inclinations, which, when they contact each other and are moved relative to each other, a force component is generated that tends to spread the legs apart.

BRIEF DESCRIPTION OF THE DRAWINGS

Further features and advantages of the invention will become apparent from the description of embodiments by means of the accompanying drawings. In the drawings:

FIG. 4 shows a perspective view from a top of a receiving part of the bone anchoring device of FIGS. 1 to 3.

FIG. 5 shows a perspective view from a bottom of the receiving part of FIG. 4.

FIG. 6 shows a top view of the receiving part of FIGS. 4 and 5.

FIG. 7 shows a cross-sectional view of the receiving part of FIGS. 4 and 5, the cross-section taken along line A-A in FIG. 6.

DETAILED DESCRIPTION

Figure 1:
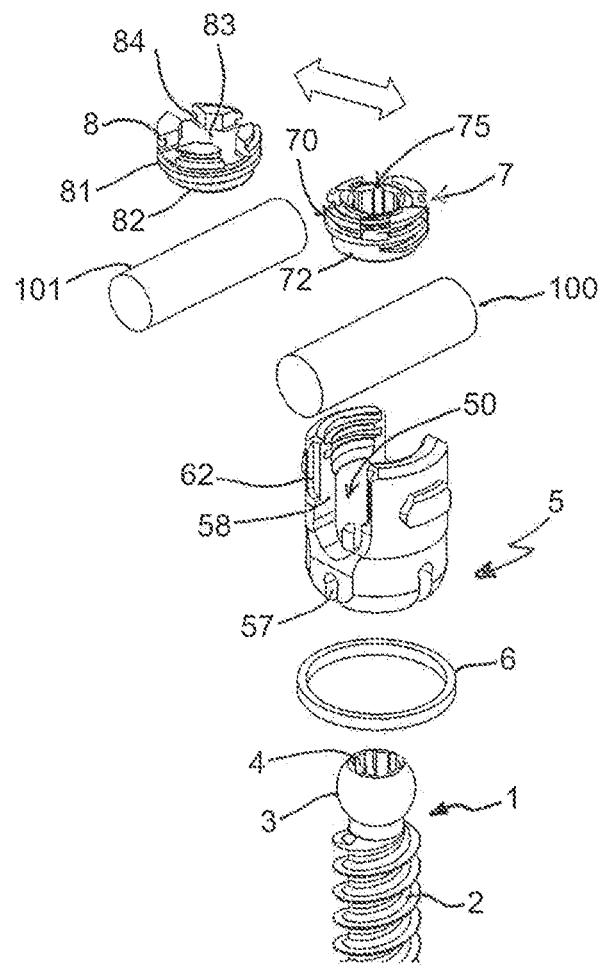
FIG. 1 shows an exploded perspective view of a first embodiment of a polyaxial bone anchoring device.
Figure 2:
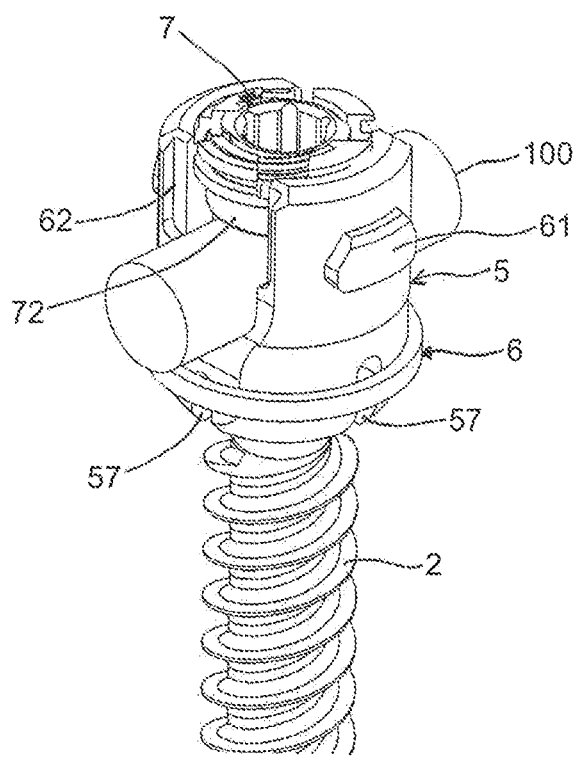
FIG. 2 shows a perspective view of the polyaxial bone anchoring device of FIG. 1 in an assembled state with an inserted rod.
Figure 3:
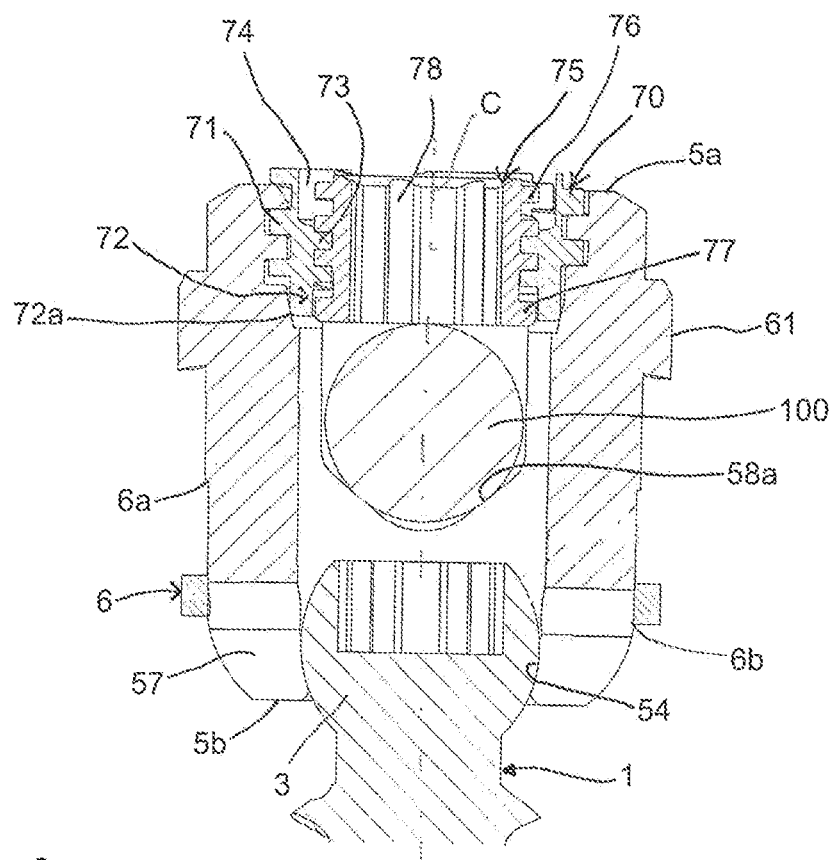
FIG. 3 shows a cross-sectional view of the polyaxial bone anchoring device of FIGS. 1 and 2, the cross-section taken in a plane including a central longitudinal axis of the receiving part and perpendicular to a rod axis of the inserted rod.

FIGS. 1 to 3 illustrate a polyaxial bone anchoring device according to a first embodiment that includes a bone anchor 1 including a shank 2 with a threaded section and a head 3. The head 3 has an outer spherical surface portion and a recess 4 at the free end for engagement with a screwdriver. The outer spherical surface portion includes a region with the greatest diameter of the sphere. The bone anchoring device further includes a receiving part 5 for receiving the head 3 of the bone anchor 1 and for receiving a rod 100 for coupling the rod 100 to the bone anchor 1. More specifically, the receiving part 5 is designed to selectively accommodate rods 100, 101 having different diameters. The bone anchoring device further includes an expansion limiting member 6 for limiting expansion of the receiving part 5. Finally, the bone anchoring device may include a locking device 7 that is configured to lock an inserted rod in the receiving part 5. More specifically, the receiving part 5 is designed such that it can be selectively used with locking devices 7, 8 that have different designs. The locking device 7, for example, may be a two-part locking device, and the locking device 8 may be a single part locking device.

Turning now additionally to FIGS. 4 to 7, the receiving part 5 may be a monolithic part that has a first or upper end 5a and an opposite second or lower end 5b. A central axis C passes longitudinally through the first end 5a and the second end 5b. The overall outer shape of the receiving part may be substantially cylindrical. A passage 50 extends from the first end 5a to the second end 5b. The passage 50 may have several sections with different diameters. In a first section 51 adjacent to the upper end 5a, the passage may be formed as a coaxial bore with a first diameter, and in a central section 52, the passage may be formed as a coaxial bore with a second diameter smaller than the first diameter. Between the first section 51 and the second section 52, there is a transition section 53 which tapers and narrows towards the second section 52 and provides an inclined surface 53a. The inclined surface 53a forms an abutment for a portion of the locking device 7, 8. Adjacent to the lower end 5b, the passage is defined by a seat 54 for the head 3. The seat 54 tapers and narrows towards the lower end 5b and has a shape such that head 3 can pivot therein. In the embodiment, the seat 54 has a spherical segment-shape to mate with the spherical shape of the head 3. However, the seat 54 may have any other shape, preferably narrowing towards the second end 5b, that enables the head 3 to pivot therein. The seat 54 opens towards the second end 5b through an opening 55. The seat 54 encompasses an inserted head 3 up to a position above the greatest diameter of the head, so that the head 3 is prevented from moving towards the upper end 5a.

A plurality of slits 57 are formed in the portion of the receiving part adjacent to the lower end 5b. The slits render the lower portion of the receiving part flexible. In greater detail, when the head 3 enters through the lower opening 55, the head receiving portion slightly expands to snap onto the head 3, until the head 3 rests in the seat 54. In the embodiment, four slits 57 are arranged at a distance of 90° from each other in a circumferential direction. The slits 57 may have a widened end portion 57a for increasing the flexibility at the lower end 5b. In the axial direction, the end portion 57a of the slits may be located above the seat 54.

For receiving the rod 100, 101, a recess 58 extends from the upper end 5a towards the lower end 5b. The recess 58 may have substantially straight side walls and a substantially V-shaped bottom forming a support surface 58a for the rod 100, 101. The support surface 58a is formed by two inclined surfaces that are oriented in a substantially triangular or angled V-shaped manner, such that an inserted rod is supported substantially along two contact lines where the rod contacts the inclined surfaces, respectively. Thus, when any of the rods 100, 101 of different diameters rests on the rod support surface, the inserted rod is inhibited from sliding in a direction transverse to the rod axis. A width of the recess 58 is such that various rods of different diameters up to a maximum diameter can be accommodated therein. The bottom of the recess 58 ends at a distance above the end portion 57a of the slits 57.

The recess 58 forms a channel for the rod. Specifically, by means of the recess 58, two open legs 59 are formed. In the first section 51 of the passage 50, the legs include an internal thread 60. The internal thread 60 may extend from the upper end 5a down to the beginning of the transition section 53. In other words, the internal thread ends above the transition section 53. A thread form of the internal thread 60 may be, for example, a square thread or a V-thread, or any other thread form.

The arrangement of the slits 57 and of the recess 58 relative to each other is such that a pair of opposite slits are aligned with the recess 58 and the other pair of opposite slits may be arranged at an angle of 90° to the longitudinal axis L of the recess 58.

Finally, at an outer surface of the receiving part 5, two opposite engagement projections 61 are formed on the legs 59, respectively. The engagement projections 61 are positioned substantially in the center of each leg in the circumferential direction and at a distance from the free end 5a. Specifically, the engagement projections 61 may have a trapezoidal outer contour, with the longer base facing in an axial direction towards the second end 5b.

More generally, the receiving part can be divided into an upper portion that includes the recess 58 and thereby forms a rod receiving portion and a lower portion that includes the seat 54 and thereby forms a head receiving portion. Due to the slits 57, the head receiving portion is expandable and permits the head 3 of the bone anchor to enter through the lower opening 55 to be seated in the seat 54. Furthermore, the head receiving portion is also compressible to clamp by friction and finally lock an inserted head 3 in the seat 54. As a pair of opposite slits 57 is at a position aligned with the recess 58, the spreading of the legs 59 causes a narrowing of the slits 57 that are aligned with the recess 58. By means of this, the head receiving portion can be compressed, which locks an inserted head 3. When the force that effects the spreading of the legs 59 is removed, the legs 59 move back to their non-spread position, thereby releasing the compression of the head receiving portion.

Moreover, the receiving part 5 has on each outer edge of the legs 59 substantially triangular-shaped or rectangularly shaped recesses 62. The recesses 62 may extend from the upper end 5a to an axial height higher than the V-shaped bottom 58a of the recess 58. The outwardly located surface 62a of each recess 62 is configured to form an abutment surface for a portion of the instrument to be described below. The abutment surface extends substantially parallel to the central longitudinal axis. The receiving part 5 has four such recesses 62, however, having at least two recesses on opposite sides from the channel formed by the recess 58 may also be possible.

Referring again to FIGS. 1 to 3, the device also includes an expansion limiting member 6 that is configured to encompass an outside of the head receiving portion. The expansion limiting member 6 in the embodiment is a ring. The ring may have an axial length that allows the ring to be moved along the head receiving portion towards the rod receiving portion to a position where the ring no longer encompasses the head receiving portion. A cross-section of the ring may be substantially rectangular with a height that is greater than a thickness of the ring. However, the ring can also have other dimensions. An inner diameter of the ring is such that when the head receiving portion is compressed, the ring can be slid from the lower end 5b onto the outside of the receiving part 5 when the head 3 is not in the seat 54, i.e., in an unloaded configuration of the receiving part. In the unloaded configuration, the ring 6 is slightly held by friction when the ring is around the head receiving portion. As shown in detail in FIGS. 3 to 5, the outer diameter of the receiving part is slightly reduced from a greater diameter in the upper portion to a smaller diameter in the lower portion of the receiving part 5, thereby forming a stop 6a. The stop 6a acts as an abutment for the ring when the ring is mounted to the receiving part 5 and moved towards the upper end 5a. An axial position of the stop 6a is in the region of the rod receiving portion of the receiving part 5. Additionally, a stop 6b is formed at a height of or slightly below the enlarged end of the slits 57. The stop 6b prevents removal of the expansion limiting member 6 towards the second end 5b once it is mounted.

The locking device 7 includes an outer locking member 70 and an inner locking member 75. The outer locking member 70 is formed as a cylindrical set screw with an external thread 71 that is configured to cooperate with the internal thread 60 on the legs 59. At a side configured to face towards the second end 5b of the receiving part, the outer locking member 70 has a substantially cylindrical thread-free portion 72. A lower outer edge 72a of the thread-free portion 72 is configured to cooperate with the inclined surface 53a in the receiving part 5. The outer edge 72a may be rounded. As shown in particular in FIG. 3, the axial length of the outer locking member 70 is such that when the outer locking member 70 is screwed between the legs 59, the outer edge 72a comes into contact with the inclined surface 53a such that a spreading force is exerted by the outer locking member 70 that tends to spread the legs 59 apart from each other. The outer locking member 70 further defines a threaded bore 73 with an internal thread which is configured to cooperate with the inner locking member 75. Moreover, on an upper side of the outer locking member 70 that is opposite to the edge 72a, a plurality of engagement recesses 74 for engagement with a drive tool may be provided.

The inner locking member 75 is formed as a set screw that is screwed into the outer locking member 70. An external thread 76 of the inner locking member 75 may have any thread form, preferably a square thread as shown in the embodiment. This may improve load distribution. At a side configured to face towards the second end 5b of the receiving part 5, the inner locking member 75 has an annular projection 77 that is configured to abut against a lowermost thread turn of the threaded bore 73. In the mounted state, this prevents inadvertent screwing of the inner locking member 75 out of the outer locking member 70. Finally, the inner locking member 75 includes a tool engagement recess 78 that may have any suitable form for a form-fit tool engagement, such as, for example, a torque-shape or hexagon-shape.

The locking device 7 is configured to effect an independent locking of the head 3 and the rod 100. With the outer locking member 70, the head 3 can be locked in the seat 54. With the inner locking member 75, the rod 100 can be locked in the recess 58.

As depicted in FIG. 1, a one part locking device 8 can be used interchangeably with the two part locking device 7, as indicated by the arrow. The one part locking device 8 may be formed as a cylindrical set screw with an external thread 81 and a thread-free lower portion 82 with an underside 85 facing the rod (see FIG. 14). The thread-free lower portion 82 has an edge 82a (see FIG. 14) that is configured to cooperate with the inclined surface 53a in the receiving part to exert a spreading force onto the legs 59. A side of the locking device 8 opposite to the thread-free portion 82 may have a structure for engagement with a drive tool. In the embodiment, a central coaxial bore 83 that extends to a distance from the underside 85 and a plurality of radial slots 84 (four in the embodiment shown) are provided. However, the shape of the engagement structure may be different to fit various tools.

The parts and portions of the bone anchoring device may be made of any material, preferably however, of titanium or stainless steel, or of any bio-compatible metal or metal alloy or plastic material. For a bio-compatible alloy, a NiTi alloy, for example Nitinol, may be used. Other materials that can be used are magnesium or magnesium alloys. Bio-compatible plastic materials that can be used may be, for example, polyether ether ketone (PEEK) or poly-L-lactide acid (PLLA). The parts can be made of the same or of different materials from one another.

Figure 8:
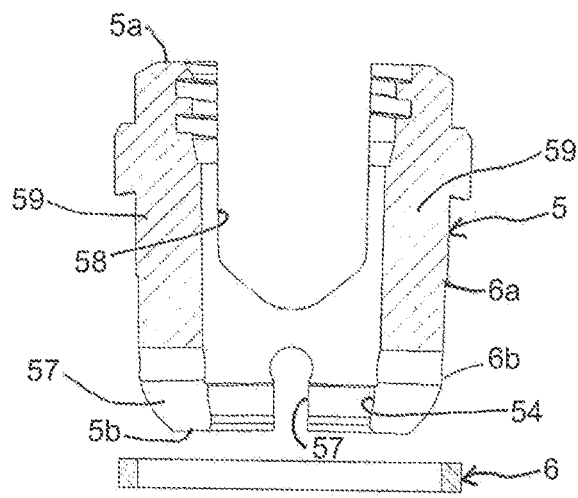
FIG. 8 shows a cross-sectional view of the receiving part with an expansion limiting member of the bone anchoring device of FIGS. 1-3 not yet mounted.
Figure 9:
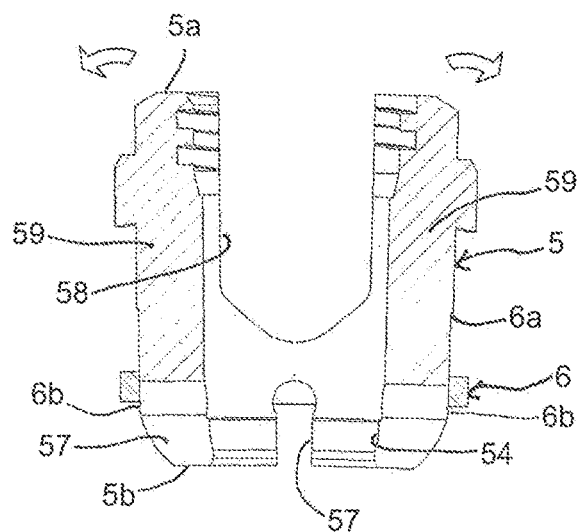
FIG. 9 shows a cross-sectional view of the receiving part depicted in FIG. 8 with the expansion limiting member at a first position around a head receiving portion of the receiving part.
Figure 10:
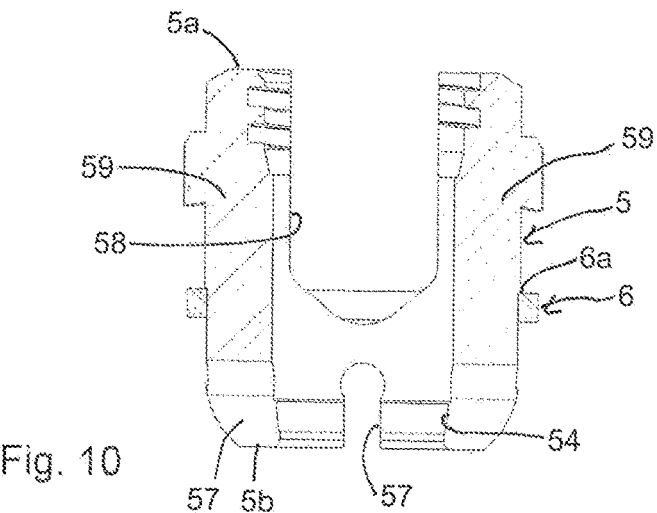
FIG. 10 shows a cross-sectional view of the receiving part of FIGS. 8 and 9 with the expansion limiting member at a second position around the head receiving portion which permits insertion of a head of a bone anchor.

FIGS. 8 to 10 illustrate the assembly of the expansion limiting member 6 in the form of the ring onto the receiving part 5. FIG. 8 shows the expansion limiting member 6 at the side of the lower end 5b of the receiving part 5 before mounting. Then, as shown in FIG. 9, the expansion limiting member is moved onto the receiving part. As an inner diameter of the ring is slightly smaller than the outer diameter of the receiving part 5 in the region of the head receiving portion in an unloaded configuration, the expansion limiting member may slightly compress the head receiving portion during mounting. As a consequence, the legs 59 are slightly spread apart. In a next step shown in FIG. 10, the expansion limiting member may be slid upward until it abuts against the stop 6a. In this position, the expansion limiting member does not compress the head receiving portion. When the expansion limiting member is above the head receiving portion, and in any case when the expansion limiting member is in an uppermost position defined by the stop 6a, the head receiving portion can be expanded to permit a head 3 of the bone anchor 1 to enter the seat 54.

Next, the assembly of the receiving part 5 with mounted expansion limiting member onto the bone anchor will be explained, with reference to FIGS. 11a to 11e. It shall be noted that these assembly steps can take place prior to implanting the polyaxial bone anchoring device in a patient's body. Alternatively, the assembly can take place when the bone anchor 1 is already inserted into bone, where the receiving part with mounted ring can then be mounted onto the head 3 that protrudes out of the bone.

Figure 11:
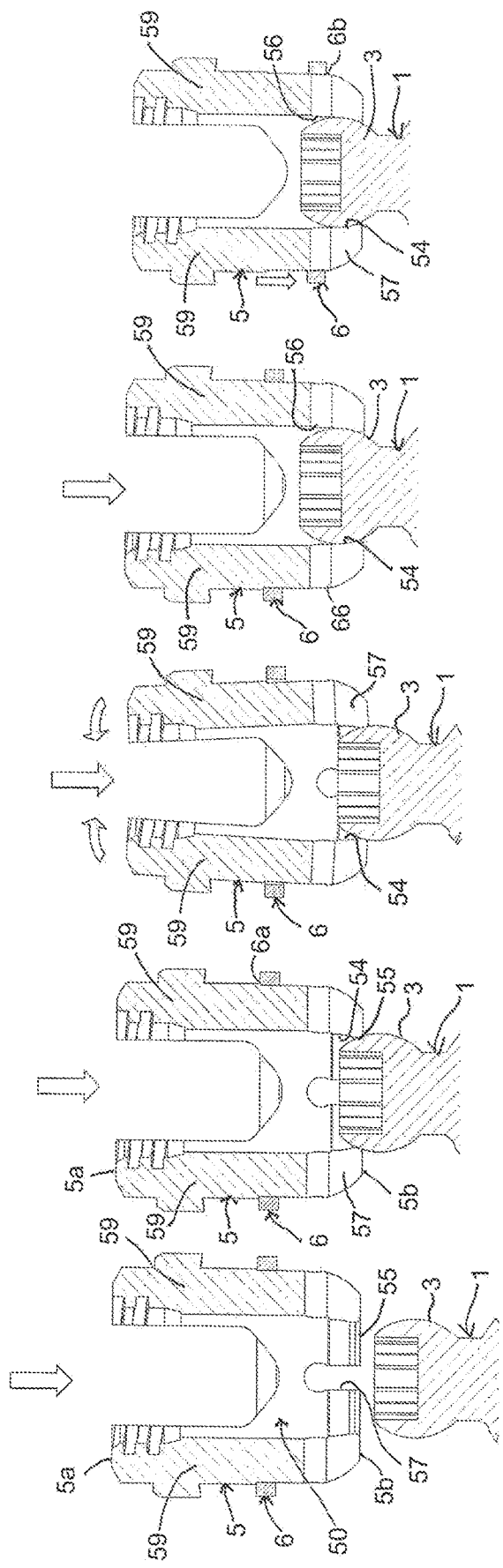
FIGS. 11a to 11e show steps of assembling the polyaxial bone anchoring device of FIGS. 1-3.

First, as shown in FIG. 11a, the head 3 of the bone anchor 1 is oriented towards the opening 55 of the receiving part 5. The expansion limiting member 6 is in the uppermost position at or near the stop 6a. As further shown in FIG. 11b, the head 3 enters through the opening 55 into the passage 50 of the receiving part 5. When the head 3 enters into the passage, the head receiving portion of the receiving part 5 is slightly expanded as shown in FIG. 11c. During the insertion, the legs 59 are slightly moved towards each other. The ring does not prevent expansion during insertion, since the ring is not around the head receiving portion. When the head 3 has been moved through the opening 55 with its region having the greatest diameter, the head 3 can rest in the seat 54 as shown in FIG. 11d. Simultaneously, the head 3 cannot move further upwards, because the seat 54 extends beyond the region with the greatest outer diameter and prevents such movement. Finally, as shown in FIG. 11e, the ring is moved downwards until it abuts against the stop 6b, so that it encompasses the head receiving portion at a correct or desired position. Due to its size, the ring exerts a small compression force onto the head receiving portion that clamps the head 3 in the seat 54 by friction. By means of this, an angular position of the bone anchor relative to the receiving part can be maintained at a desired angular position before final locking of the head. Simultaneously, the expansion limiting member prevents removal of the head 3 through the lower opening. Thereby, the head is pre-locked in the receiving part 5. In the configuration shown in FIG. 11e, several correction steps with respect to the bones, bone parts or vertebrae in which the polyaxial bone anchoring device is or will be implanted, can be carried out.

Figure 12:
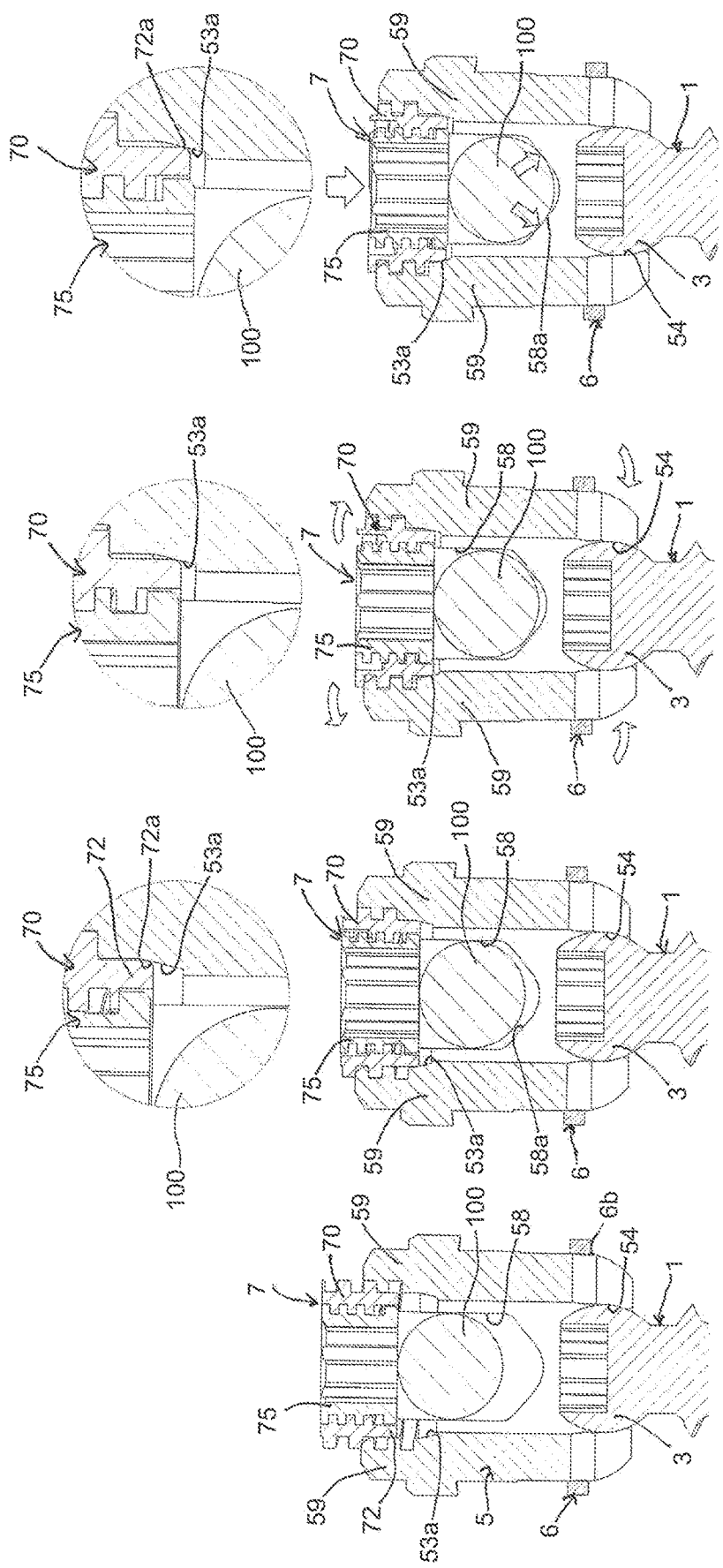
FIGS. 12a to 12d show cross-sectional views of steps of locking the polyaxial bone anchoring device of FIGS. 1-3, with FIGS. 12b to 12d also depicting enlarged partial views of each of the respective steps.

Referring now to FIGS. 12a to 12d, the locking of the polyaxial bone anchoring device will be described. As shown in FIG. 12a, the rod 100 is inserted into the recess 58, and the locking device 7 is also inserted through the upper end 5a. In the example shown, the rod 100 has a diameter such that the rod may touch the sidewalls of the channel.

Next, for FIGS. 12b to 12d, enlarged views of the engagement between the edge 72a of the locking device 7 and the inclined surface 53a of the receiving part 5 are separately depicted above each of the figures. In FIG. 12b, the locking device is screwed-in further and moves the rod towards the rod support surface 58a. The edge 72a of the locking device 7 comes into contact with an upper region of the inclined surface 53a. Next, as depicted in FIG. 12c, when the edge 72a moves further along the inclined surface 53a, an outwardly directed force component is generated that spreads the legs 59 apart, as indicated by the arrows above the receiving part 5. Simultaneously, the head receiving portion is compressed around the inserted head 3. This is indicated by the arrows in the lower portion of the receiving part 5. The ring is still held by friction and encompasses the head receiving portion. When the compression force onto the head is such that the head is locked, the legs may not spread further. Finally, as shown in FIG. 12d, in a configuration in which the head 3 is locked by the compression of the head receiving portion, the rod 100 can be locked separately with the inner locking member 75 by screwing the inner locking member 75 downwards so that the inner locking member 75 exerts a locking force onto the rod 100. This results in force components indicated by the inclined arrows in FIG. 12d that further add to the forces that spread apart the legs, which contributes to an additional locking force onto the head.

Figure 13:
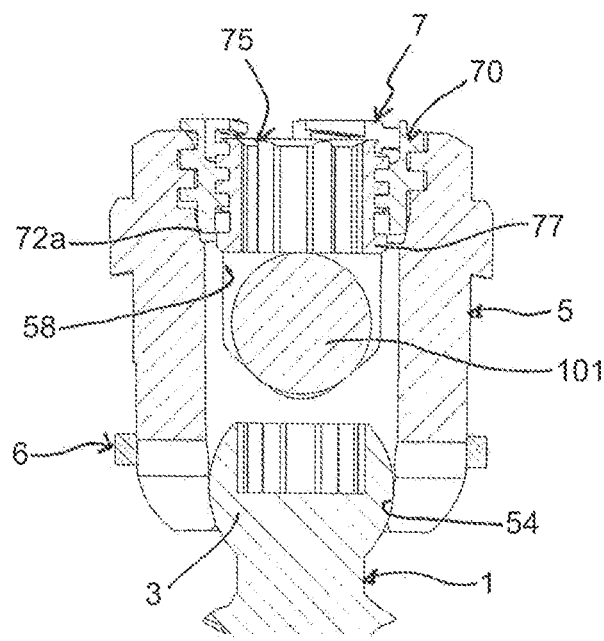
FIG. 13 shows a cross-sectional view of the polyaxial bone anchoring device according to FIGS. 1 to 12d with a two-part locking device and an inserted rod having a first diameter.

With the two-part locking device 7, rods of different diameter can be fixed. As illustrated in FIG. 13, the rod 101 which has a smaller diameter than the rod 100 previously described, is inserted. The fixing of the rod in the recess 58 can be achieved by screwing the inner locking element 75 towards the rod 101 until the inner locking member 75 presses onto the upper surface of the rod 101. The locking of the head 3 is effected in the same manner as described with reference to FIGS. 12a to 12d. Hence, with the two-part locking device 7, the versatility of the polyaxial bone anchoring device is considerably increased.

Figure 14:
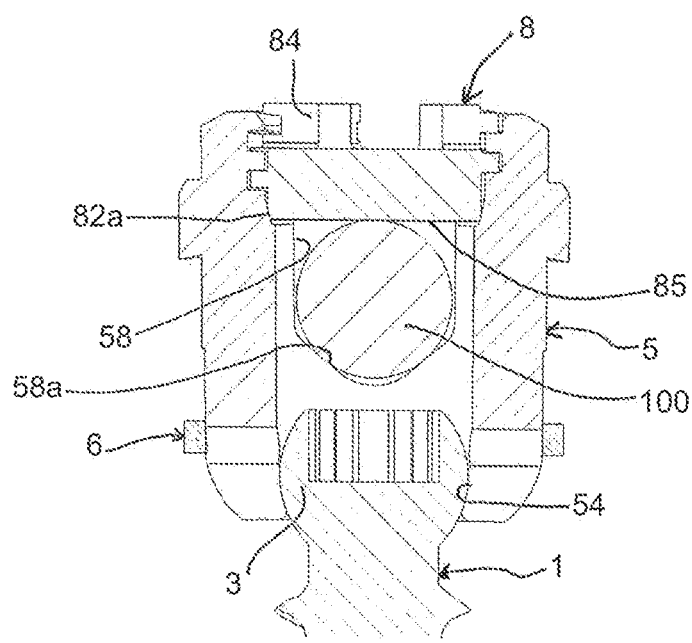
FIG. 14 shows a cross-sectional view of the polyaxial bone anchoring device of FIGS. 1 to 12d with a single part locking device and a rod having a second diameter greater than the first diameter.

FIG. 14 illustrates the use of the bone anchoring device with the rod 100 having a greater diameter than the rod 101 and the single part locking device 8. The single part locking device is configured to be used with a rod of a specific diameter. When the locking device 8 is screwed between the legs 59, the edge 82a comes into contact with the inclined surface 53a, thereby spreading the legs 59 apart, and in turn compressing the head receiving portion and locking the head 3. At the same time, the lower surface 85 of the locking device 8 comes into contact with the upper surface of the rod 100 and presses the rod 100 towards the rod support surface 58a to fix the position of the rod.

It shall be noted that in spite of the spreading of the legs 59 during locking of the head, the locking device 7, 8 is able to lock the whole device, and for example, does not come loose.

In use, two or more bone anchoring devices are inserted into vertebrae, for example, the pedicles of vertebrae, or other bone parts, and are connected via a rod. A multiplicity of adjustment and correction steps can be carried out and facilitated using the polyaxial bone anchoring device described above.

Referring now to FIGS. 15 to 19, an instrument will be described that can be provided together with the polyaxial bone anchoring device as a system.

Figure 15:
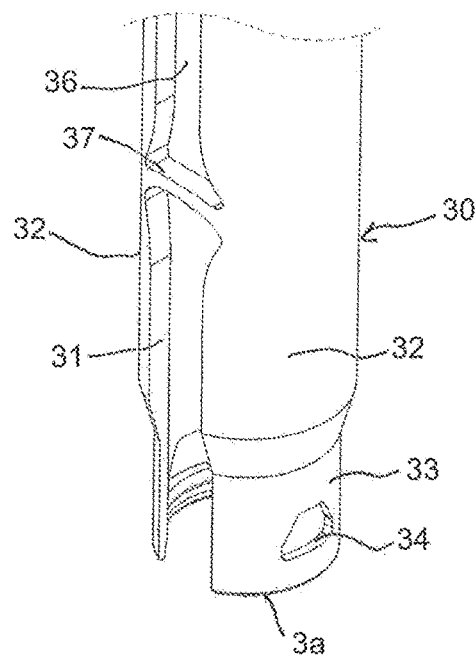
FIG. 15 shows a front portion of an outer sleeve of an instrument configured to be used with the bone anchoring device of FIGS. 1 to 14.
Figure 16:
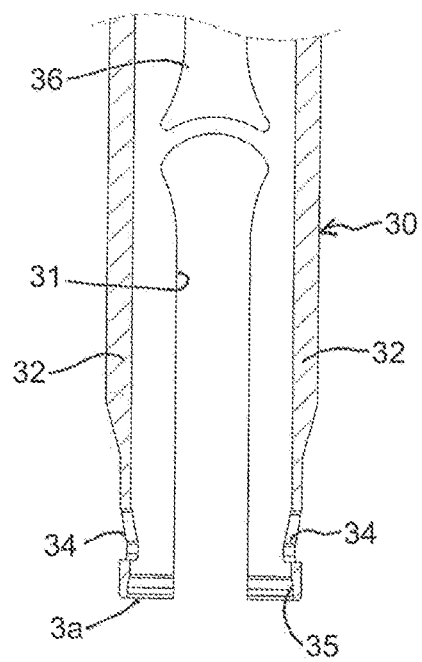
FIG. 16 shows a cross-sectional view of the outer sleeve of FIG. 15, the cross-section being taken in a plane including the sleeve axis and extending through centers of arms formed by an elongate recess in the outer sleeve.
Figure 17:
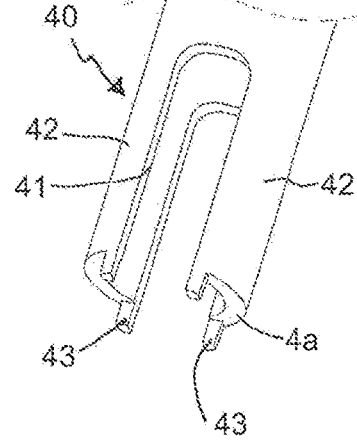
FIG. 17 shows a perspective view of a front portion of an inner sleeve of the instrument to be used with the bone anchoring device of FIGS. 1 to 14.
Figure 18:
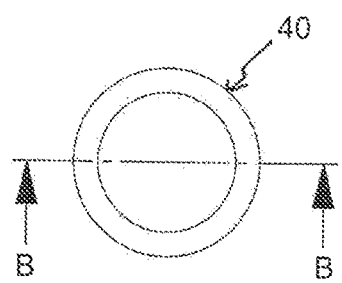
FIG. 18 shows a top view of a rear end of the inner sleeve shown in FIG. 17.
Figure 22:
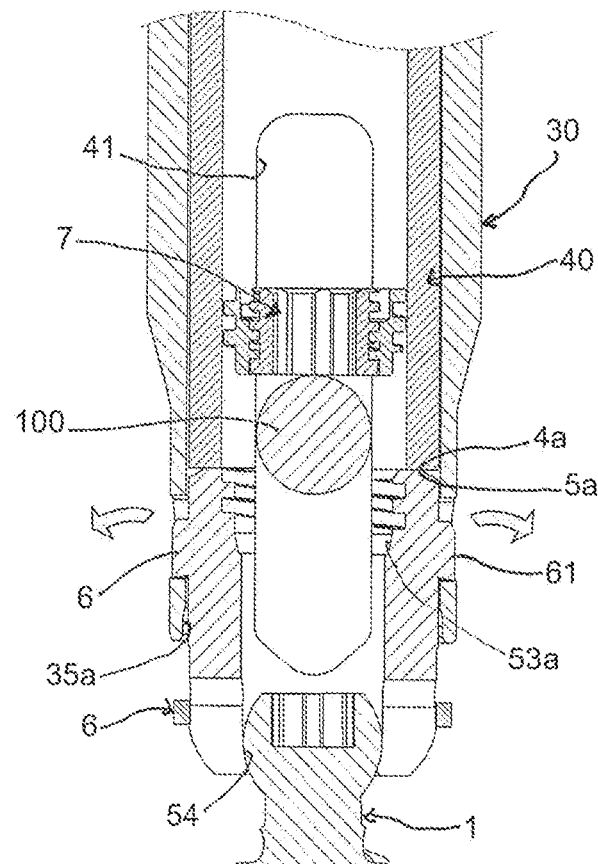
FIG. 22 shows a cross-sectional view of the instrument mounted to the bone anchoring device, with an inserted head of a bone anchor and inserted rod and locking element, the cross-section including the central longitudinal axis of the receiving part and perpendicular to the rod axis of the inserted rod.

The instrument includes an outer sleeve 30 and an inner sleeve 40. Although only front portions of the outer sleeve 30 and the inner sleeve 40 are shown in the figures, the outer sleeve 30 and the inner sleeve 40 also have opposite end portions and a mechanism to displace the inner sleeve relative to the outer sleeve. Referring in greater detail to FIGS. 15, 16, and 22, the outer sleeve 30 is designed to be placed onto the receiving part 5 while the rod is in the recess 58. To permit this, the outer sleeve has a recess 31 that extends from a front end 3a to a distance therefrom. By the recess 31, two opposite arms 32 are formed. The width and depth of the recess is such that when the outer sleeve engages the receiving part, the recess matches the width of the rod recess 58 of the receiving part or has a greater width. By means of this, the rod 100 can extend through the recess 31 and move therein along the rod axis and in an axial direction of the bone anchoring device. An inner diameter of the outer sleeve 30 is such that the outer sleeve 30 can engage the outer surface of the receiving part 5. The recess 31 also facilitates snapping of the outer sleeve onto the receiving part, whereby the arms 32 are slightly spread apart. A second recess 36 may be provided above the recess 31, the second recess also extending in a longitudinal direction and being separated from the recess 31 by a bridge 37. The recess 36 may render the front portion of the outer sleeve more flexible.

Adjacent to the front end 3a of the outer sleeve 30, there is an engagement section 33 that has a cutout 34 which is sized and shaped such that the projections 61 on the outer surface of the legs 59 can extend therein or therethrough. The projections 61 and the cutouts 34 provide a form-fit connection between the outer sleeve and the receiving part 5. Moreover, adjacent to the front end 3a, there may be a section 35 with a slightly greater inner diameter compared to the outer diameter of the receiving part 5. As shown in FIG. 22, a small gap 35a is formed between the outer surface of the receiving part 5 and the inner surface of the outer sleeve 30. The gap 35a provides space for a slight outward movement of the legs. Also, the gap 35a may facilitate detaching of the outer sleeve when the instrument is removed.

The inner sleeve 40 has a front end 4a and an inner diameter such that when the inner sleeve is placed within the outer sleeve 30 onto the receiving part 5, the front end 4a can rest on the upper end 5a of the receiving part 5. From the front end 4a, a substantially rectangular or U-shaped recess 41 extends towards the rear end (not shown). The recess 41 divides the front portion of the inner sleeve 40 into two arms 42. The size and depth of the recess 41 is such that the inner sleeve can be placed over a rod 100, as shown in FIG. 22. More specifically, a width of the recess 41 corresponds to a width of the recess 58 of the receiving part.

Figure 19:
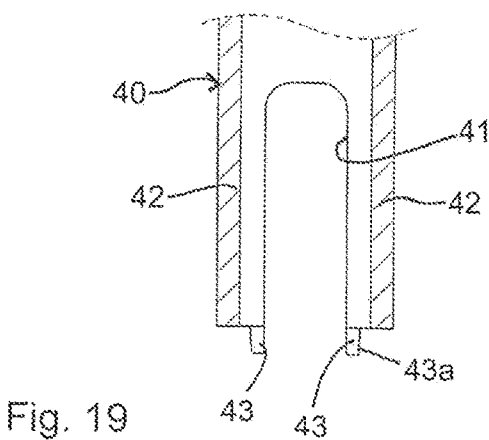
FIG. 19 shows a cross-sectional view of the front portion of the inner sleeve of FIGS. 17 and 18, the cross-section taken along line B-B in FIG. 18.
Figure 21:
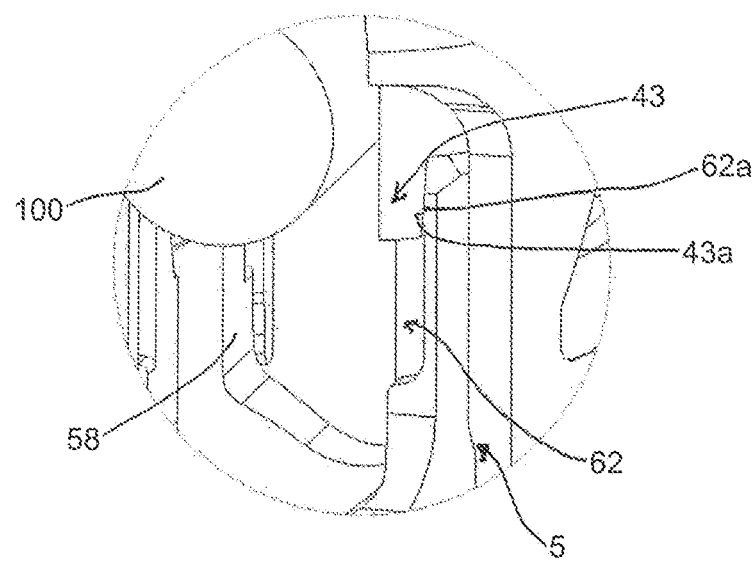
FIG. 21 shows an enlarged portion of FIG. 20c, depicting cooperating surfaces of the instrument and the receiving part more in detail.

On either end of the arms 42, longitudinal projections 43 are provided that extend from the front end 4a. More specifically, four projections 43 are formed, each being adjacent to the U-shaped recess 41. The projections 43 are configured to engage the recesses 62 provided at the outer edge of the legs 59 of the receiving part 5. As best seen in FIGS. 19 and 21, a surface 43a of each projection 43 which faces away from the U-shaped recess 41 is inclined in a manner such that the thickness of the projection 43 increases from the free end of the projection towards the front end 4a of the inner sleeve 40. The inclined surface 43a is configured to come into engagement with the outwardly located surface 62a of the recess 62 on the legs 59. As the inclined surface 43a is inclined with respect to the substantially vertical surface 62a, the projections 43 exert a spreading force component onto the legs 59 of the receiving part 5. The engagement therefore tends to spread the legs apart.

Figure 20C:
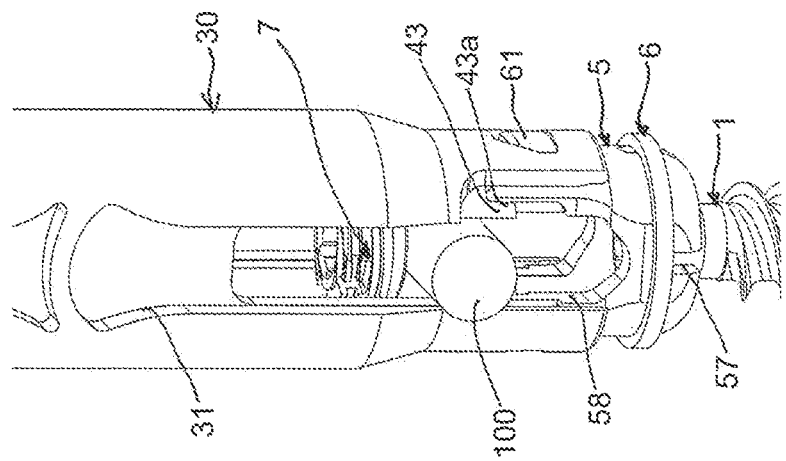
FIGS. 20a to 20c show steps of attaching the instrument of FIGS. 15 to 19 to the bone anchoring device of FIGS. 1 to 14 and of spreading the legs of the receiving part.
Figure 20B:
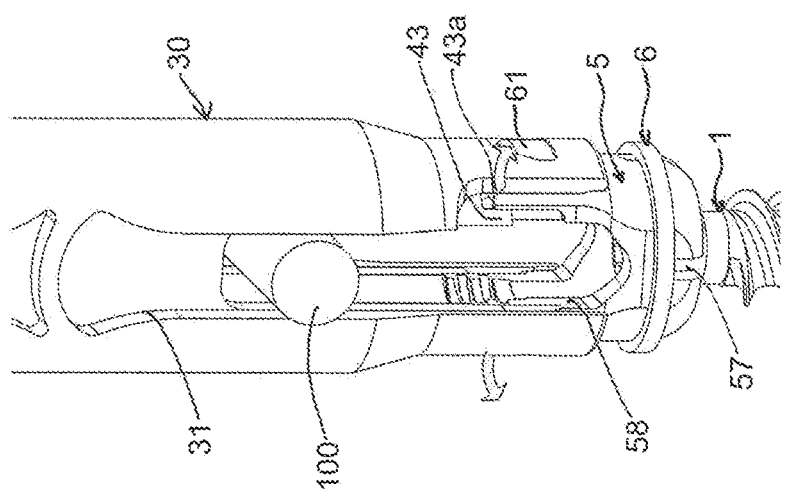
Figure 20A:
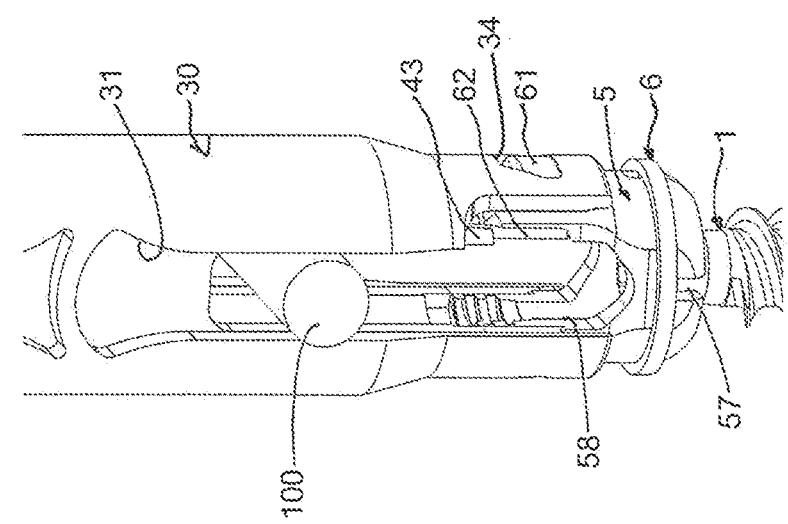

Referring to FIGS. 20*a* to 20*c*, use of the polyaxial bone anchoring device with the instrument will be described. In a first step, shown in FIG. 20*a*, the outer sleeve 30 is mounted to the receiving part 5. The engagement portion 33 snaps over the projections 61 to form a form-fit connection between the outer sleeve and the receiving part. The recess 31 is aligned with the recess 58 in the receiving part. Also, the inner sleeve 40 is oriented such that the recess 41 is aligned with the recess 58 of the receiving part 5. The front end 4*a* of the inner sleeve does not yet touch the upper end 5*a* of the receiving part, nor do the projections 43 press against the surface 62*a* of the recess 62. In this configuration, the head is maintained by friction in a desired angular position and can be pivoted by overcoming the friction force, for example, manually. Also, the head is safely locked in the seat since the expansion limiting member 6 limits expansion of the head receiving portion so that the head cannot escape. The rod 100 may be at a high position, away from the bottom of the recess 58. This allows various surgical steps to be performed, such as, for example, pulling the vertebra or bone part in which the bone anchor is anchored towards the rod 100.

Next, as shown in FIG. 20*b*, the inner sleeve 40 is moved down until the inclined surface 43*a* of the projection 43 comes into contact with the outwardly located surface 62*a* of the recess 62, thereby spreading apart the legs 59 of the receiving part 5. The projections 61 can enter slightly deeper into the cutouts 34 of the outer sleeve 30. Moreover, the enlarged diameter section 35 of the outer sleeve 30 which forms the gap between the outer sleeve and the receiving part provides space for the slight spreading of the legs. When the legs are spread apart, the head is locked by the compression of the head receiving portion.

Finally, as shown in FIG. 20*c*, the locking device can be inserted through the inner sleeve 40. The rod 100 and the locking device are further moved downward, and the locking device spreads the legs to maintain the locking of the head 3. Lastly, the instrument can be removed.

FIG. 21 depicts in greater detail the engagement of the inclined surface 43*a* with the outwardly located surface 62*a*, which results in the spreading of the legs to compress the head receiving portion. FIG. 22 shows a cross-sectional view of the configuration of FIG. 20*c*, which illustrates in particular the abutment of the front end 4*a* of the inner sleeve at the upper end 5*a* of the receiving part.

Figure 23:
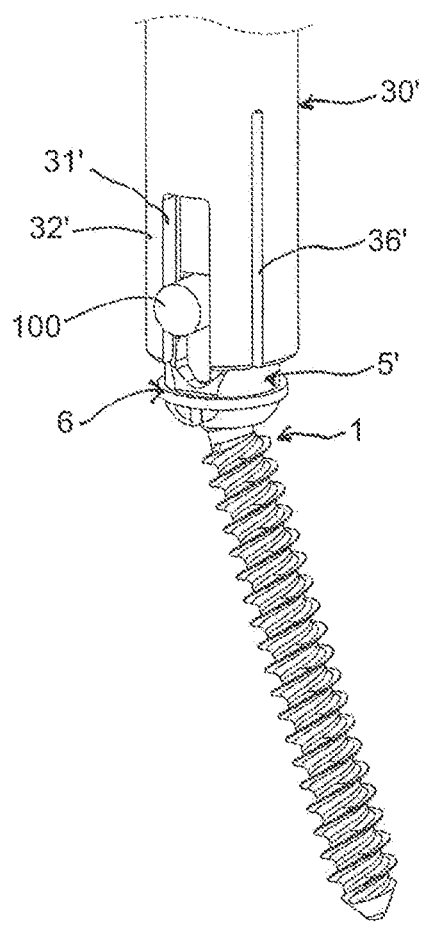
FIG. 23 shows a perspective view of a second embodiment of an instrument to be used together with the polyaxial bone anchoring device of the first embodiment.
Figure 24:
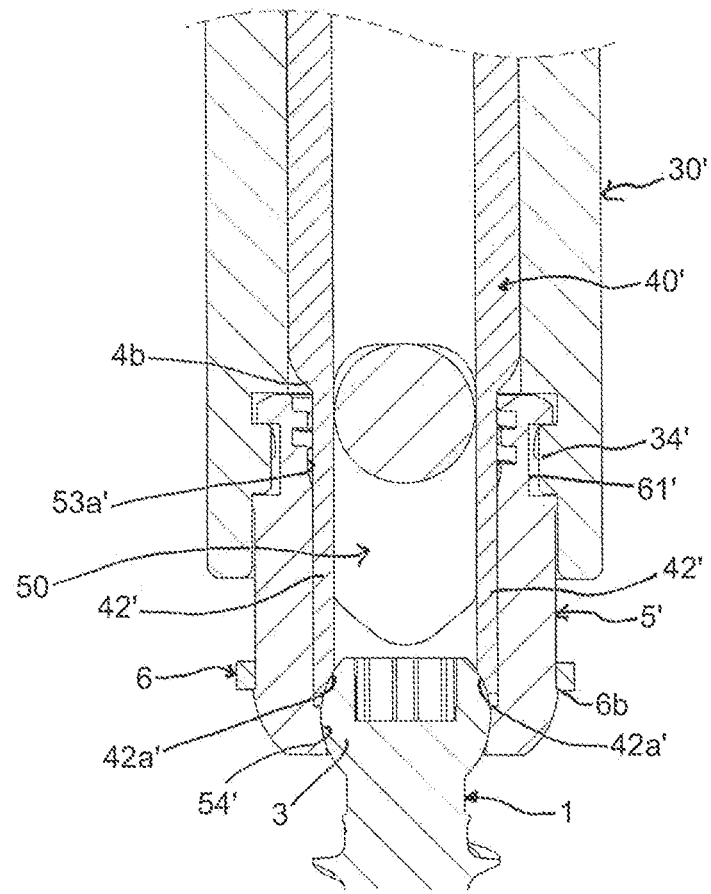
FIG. 24 shows a cross-sectional view of a system including the polyaxial bone anchoring device of the first embodiment and the instrument according to the second embodiment, the cross-section taken in a plane including the central longitudinal axis of the receiving part and perpendicular to the rod axis of the inserted rod.

Turning now to FIGS. 23 and 24, a second embodiment of the instrument will be described. Also, the polyaxial bone anchoring device is slightly modified. Identical or substantially similar portions are marked with the same reference numerals as in the previous embodiment. As can be seen in particular in FIG. 24, the projections 61 are omitted. Instead, recesses 61' are provided on the legs for engagement with the instrument. The instrument includes an outer sleeve 30' with a recess 31' for the rod, forming two arms 32' which have inwardly oriented projections 34' that are configured to engage the recesses 61'. An additional recess 36' may be provided for enhancing the flexibility of the arms. The inner sleeve 40' defines the substantially U-shaped recess 41 and has, in the region of the arms 42', a reduced outer diameter so that the arms 42' are configured to extend into the passage 50 of the receiving part. The arms 42' have a length such that when the inner sleeve 40' abuts with the upper portion 4*b* against the free end 5*a*, the arms 42' press with their free end surface 42*a*' onto an inserted head 3. The free end surface 42*a*' may have a spherical shape that matches the spherical shape of the head.

In use, the inner sleeve 40' temporarily locks the head 3 in the seat 54'. When the inner sleeve 40' is retracted, the head can pivot again in the seat. Thus, with the instrument, it is possible to provisionally lock the head 3 with only the instrument. The polyaxial bone anchoring device is finally locked by inserting a locking device 7, 8 after removal of the instrument.

Figure 25:
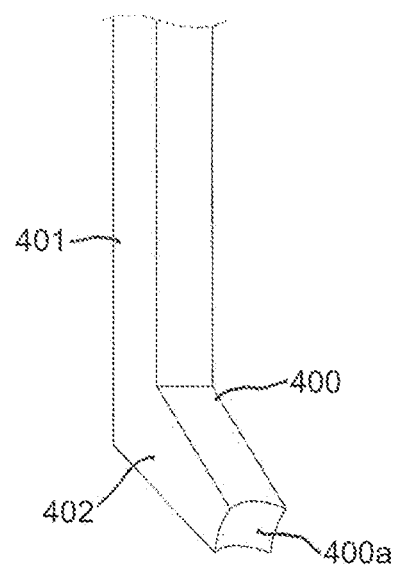
FIG. 25 shows a perspective view of a front portion of a third embodiment of an instrument to be used together with the polyaxial bone anchoring device.
Figure 26:
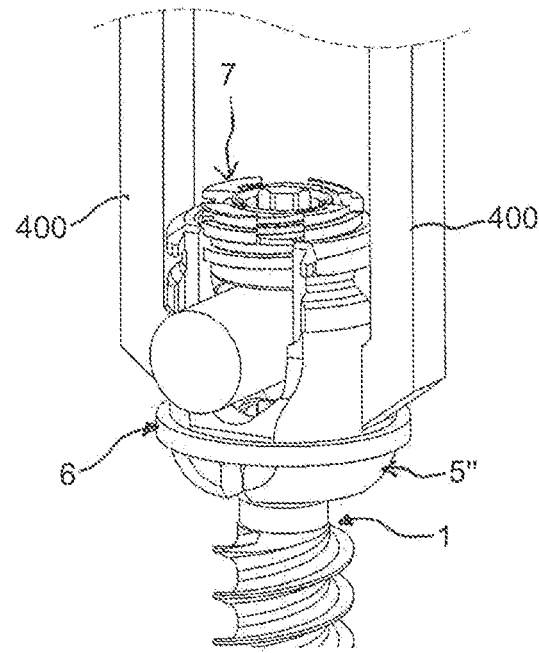
FIG. 26 shows a perspective view of the instrument of FIG. 25 attached to a bone anchoring device according to a modified embodiment.
Figure 27:
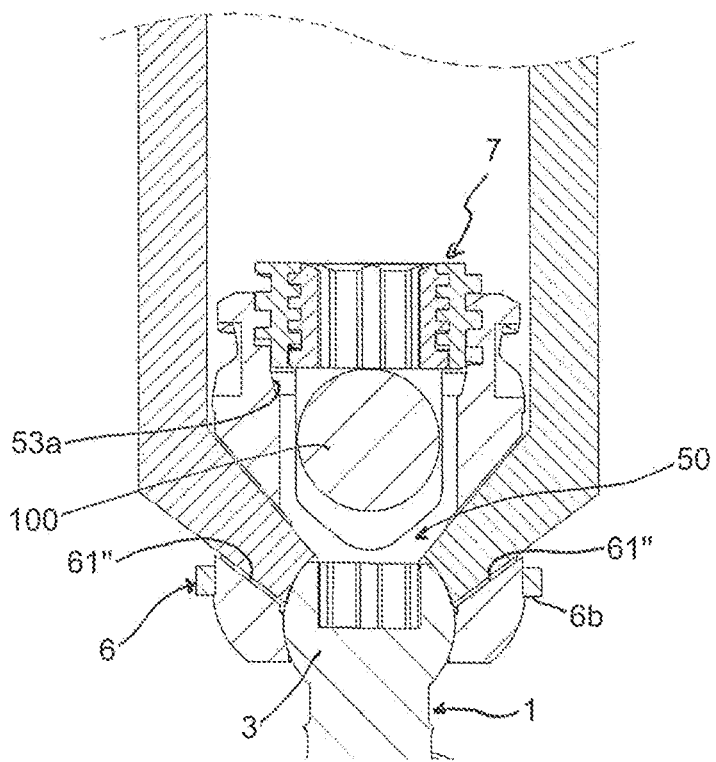
FIG. 27 shows a cross-sectional view of a system including the instrument and the bone anchoring device of FIG. 26, wherein the cross-section is taken in a plane including the central longitudinal axis of the receiving part and perpendicular to the rod axis of the inserted rod.

A further embodiment of the instrument is shown in FIGS. 25 to 27. For this instrument, the receiving part 5" is slightly modified, in that the receiving part 5" defines recesses 61" for engaging the head with the instrument laterally from the outside of the receiving part. The shape of the recesses is adapted to the shape of the instrument. In the example shown, the recesses 61" have a rectangular cross-section that increases in width from the passage 50 towards the outside of the receiving part 5". The recesses 61" are inclined to permit guiding through by plier-like arms 400 of an instrument. The plier-like arms shown in the figures have a straight or vertical portion 401 and an inclined portion 402 with a spherically-shaped end surface 400*a*. Each arm 400 is configured to extend with the inclined portion 402 through the recess 61" and to press with the end surface 400*a* onto an inserted head 3. The instrument also includes an actuating mechanism (not shown) which actuates the arms 400 to enter the recesses and press onto the head and/or to release the head and be removed from the recesses 61". Hence, the actuating mechanism functions in a plier-like manner. With this instrument it is possible to engage the head and temporarily lock the head in the receiving part, and to simultaneously permit the insertion of the locking device 7, 8. In use, after temporary locking of the head, the instrument is removed, and the rod can be finally locked with the locking device, similarly as with the first embodiment.

Further modifications of the embodiments described are also possible. In addition, the features of one embodiment can also be combined with those of another embodiment to produce a variety of still further embodiments. The parts are not limited to their detailed shapes as described in the embodiments.

While the bone anchoring devices have been described and are shown as bottom loading bone anchoring devices, where the bone anchor is inserted from the bottom end of the receiving part, the invention can also be used with a top loading bone anchoring device where the bone anchor is inserted from the top end of the receiving part.

While the rod is shown as a rigid rod with a smooth surface, the term "rod" shall mean any elongate connection member that is configured to be received in the rod receiving portion of the receiving part and that is configured to be fixed by a locking device in the rod receiving portion. In particular, various shapes, diameters, surface properties, etc., shall be encompassed within the scope of the invention.

Various other modifications may be made without departing from the scope of the invention. In particular, the recesses 62 in the first embodiment can be omitted. The receiving part is also not limited to the specific shapes described in the embodiments. While the receiving part is shown as a monolithic part, other receiving parts can instead be made up of two or more pieces. The number and shape of the slits can also vary. The outer shape of the receiving part can also be different. The expansion limiting member can also be different from a ring, for example, in some embodiments, the expansion limiting member can be two clamp-like half rings that are mounted from opposite sides and fixed to the receiving part.

In addition, for the bone anchor, all kinds of bone anchors can be used, such as screws, nails, etc.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A bone anchoring device for coupling a rod to a bone anchor, the bone anchoring device comprising:
   a locking device;
   a receiving part having a first end and a second end below the first end, the receiving part comprising:
      a head receiving portion at the second end defining a seat for pivotably receiving a head of the bone anchor, wherein the head receiving portion is expandable to permit insertion of the head into the seat and compressible to lock the head in the seat; and
      a rod receiving portion above the head receiving portion that defines a recess for receiving the rod, the recess forming two legs each having an engagement surface for engaging the locking device to lock the rod in the recess, wherein when the locking device is advanced axially in the recess, the legs are urged radially outwardly and the head receiving portion is urged radially inwardly for compressing and locking the head; and
   an expansion limiting member mountable to the receiving part from the second end and positionable entirely above a bottom of the recess for the rod, the expansion limiting member comprising a surface configured to engage a portion of the receiving part spaced apart from the engagement surfaces of the legs, and where the receiving part comprises a first stop for limiting axial movement of the expansion limiting member towards free ends of the legs;
   wherein when the expansion limiting member is mounted to the receiving part, the expansion limiting member is adjustable from a first configuration relative to the receiving part where the head receiving portion is expandable to permit the insertion of the head, to a second configuration where the expansion of the head receiving portion is restricted, wherein at the second configuration, the entire expansion limiting member is positioned below the bottom of the recess for the rod and a second stop restricts downward movement of the expansion limiting member relative to the receiving part.

2. The bone anchoring device of claim 1, wherein the expansion limiting member comprises a ring.

3. The bone anchoring device of claim 1, wherein when the expansion limiting member is at the second configuration, the expansion limiting member is configured to exert a compression force onto the head receiving portion such that an angular position of the head relative to the receiving part is held by friction.

4. The bone anchoring device of claim 1, wherein the expansion limiting member is movable axially between the first configuration and the second configuration.

5. The bone anchoring device of claim 1, wherein the rod receiving portion comprises a second engagement surface engageable by a spreading member for urging the legs radially outwardly.

6. The bone anchoring device of claim 5, wherein the second engagement surface is inclined and widens towards free ends of the legs.

7. The bone anchoring device of claim 5, wherein the second engagement surface is provided at at least one of the legs.

8. The bone anchoring device of claim 5, wherein the spreading member is formed on the locking device and is configured to engage the second engagement surface to urge the legs radially outwardly when the locking device is advanced axially in the recess.

9. The bone anchoring device of claim 1, wherein the seat is configured to limit axial movement of the head towards the rod receiving portion.

10. The bone anchoring device of claim 1, wherein a rod support surface having a substantially V-shaped cross-section is formed at a bottom of the recess for the rod for interchangeably supporting rods with different diameters.

11. The bone anchoring device of claim 1, wherein the receiving part comprises a channel configured to provide access for an instrument to directly contact the head while the rod is inserted in the recess.

12. The bone anchoring device of claim 1, wherein the receiving part is a monolithic part.

13. The bone anchoring device of claim 1, wherein the rod directly engages a surface defining the recess for the rod when the rod is locked in the recess.

14. A method for coupling a rod to a bone using a bone anchoring device comprising a bone anchor comprising a shank and a head, a locking device, a receiving part having a first end and a second end below the first end, the receiving part comprising a head receiving portion at the second end defining a seat for pivotably receiving the head, wherein the head receiving portion is expandable to permit insertion of the head into the seat and compressible to lock the head in the seat, and a rod receiving portion above the head receiving portion that defines a recess for receiving the rod, the recess forming two legs each having an engagement surface for engaging the locking device to lock the rod in the recess, wherein when the locking device is advanced axially in the recess, the legs are urged radially outwardly and the head receiving portion is urged radially inwardly for compressing and locking the head, and an expansion limiting member mountable to the receiving part from the second end and positionable entirely above a bottom of the recess for the rod, the expansion limiting member comprising a surface configured to engage a portion of the receiving part spaced apart from the engagement surfaces of the legs, and where the receiving part comprises a first stop for limiting axial movement of the expansion limiting member towards free ends of the legs, wherein when the expansion limiting member is mounted to the receiving part, the expansion limiting member is adjustable from a first configuration relative to the receiving part where the head receiving portion is expandable to permit the insertion of the head, to a second configuration where the expansion of the head receiving portion is restricted, wherein at the second configuration, the entire expansion limiting member is positioned below the bottom of the recess for the rod and a second stop restricts downward movement of the expansion limiting member relative to the receiving part, the method comprising:
   anchoring the shank of the anchoring element to bone;

adjusting an angular position of the receiving part relative to the shank when the head is held in the seat;

inserting the rod into the recess;

engaging the locking device with the engagement surface on the legs; and advancing the locking device in the receiving part to lock the rod relative to the receiving part and to lock the angular position of the receiving part relative to the shank.

15. The method of claim 14, further comprising inserting the head into the head receiving portion when the expansion limiting member is at the first configuration, and adjusting the expansion limiting member from the first configuration to the second configuration to restrict expansion of the head receiving portion and removal of the head.

16. A bone anchoring device for coupling a rod to a bone, the bone anchoring device comprising:
a bone anchor comprising a shank and a head; and
a receiving part having a first end and a second end below the first end, the receiving part comprising:
a rod receiving portion at the first end having a first surface that defines a recess for receiving the rod, the recess forming two legs; and
a head receiving portion at the second end that defines a seat for pivotably receiving the head of the bone anchor and a plurality of slits that render the head receiving portion expandable to permit insertion of the head into the seat and compressible to lock the head in the seat, wherein each of the slits is open to the second end of the receiving part and has a closed end towards the first end of the receiving part, and wherein an axial height of each of the slits is greater than both a maximum width of the entire slit measured perpendicular to the axial height and a minimum axial distance between the slit and the recess for the rod;
wherein at least part of a first one of the slits is aligned circumferentially with at least part of the recess for the rod, such that when the legs are urged radially outwardly, the head receiving portion is urged radially inwardly for compressing and locking the head, while a second one of the slits is entirely spaced apart from the recess for the rod in the circumferential direction;
wherein the bone anchoring device is adjustable to a first configuration where the head receiving portion is expandable to permit the insertion of the head;
wherein the bone anchoring device is adjustable to and configured to maintain a second configuration where a compression force is exerted onto the head receiving portion to restrict the expansion of the head receiving portion, and where an angular position of the head relative to the receiving part is held by friction but remains adjustable when a force greater than a force of the friction is applied to the bone anchor or the receiving part, while the recess for the rod remains sufficiently unobstructed for the rod to extend and move therethrough; and
wherein when the angular position of the head relative to the receiving part is locked, a portion of the first surface of the rod receiving portion that faces the first end of the receiving part is configured to directly contact the rod to lock the rod in the recess.

17. The bone anchoring device of claim 16, further comprising an expansion limiting member configured to exert the compression force onto the head receiving portion when the bone anchoring device is at the second configuration.

18. The bone anchoring device of claim 17, wherein the expansion limiting member is configured to engage a different portion of the receiving part at the first configuration.

19. The bone anchoring device of claim 17, wherein the expansion limiting member is positionable around at least part of the head receiving portion.

20. The bone anchoring device of claim 17, wherein the expansion limiting member comprises a ring.

21. The bone anchoring device of claim 16, further comprising a locking device, wherein the two legs each has an engagement surface for engaging the locking device to lock the rod in the recess, and wherein the bone anchoring device is adjustable to and configured to maintain the second configuration while the locking device is disengaged from the engagement surfaces of the legs.

\* \* \* \* \*